United States Patent [19]

Fuisz

[11] Patent Number: 5,773,429
[45] Date of Patent: Jun. 30, 1998

[54] DRUG COMBINATION FOR TREATING CALCIUM LOSS

[75] Inventor: Richard C. Fuisz, McLean, Va.

[73] Assignee: Fuisz Technologies Ltd., Chantilly, Va.

[21] Appl. No.: 762,672

[22] Filed: Dec. 11, 1996

[51] Int. Cl.$^6$ .................. A61K 31/66; A61K 31/445
[52] U.S. Cl. ............................... 514/102; 514/327
[58] Field of Search ..................... 514/327, 102

[56] References Cited

U.S. PATENT DOCUMENTS

| | | | |
|---|---|---|---|
| 4,705,651 | 11/1987 | Staibano | 260/502.5 C |
| 4,962,115 | 10/1990 | Van Daele | 514/326 |
| 5,270,365 | 12/1993 | Gertz et al. | 514/108 |
| 5,464,632 | 11/1995 | Cousin et al. | 424/465 |

OTHER PUBLICATIONS

De Groen et al. "Esophagitis Associated with the Use of Alendronate", N Engl. J. Med. 335:1016–21, 1996.

Reyntjens et al. (1986), "Development and Clinical Use of the New Gastrointestinal Prokinetic Drug Cisapride," *Drug Development Research,* vol. 8, pp. 251–265.

Reyntjens et al. (1984), "New Approach to Gastrointestinal Motor Dysfunction: Non–Antidopaminergic, Non–Cholinergic Stimulation with Cisapride," *Current Therapeutic Reasearch,* vol. 36, pp. 1029–1037.

Van Daele et al. (1986), "Synthesis of Cisapride, a Gastrointestinal Stimulant Derived From Cis–4–Amino–3–Methoxypiperidine," *Drug Development Research,* vol. 8, pp. 225–232.

*Primary Examiner*—Raymond Henley, III
*Attorney, Agent, or Firm*—Sandra M. Nolan

[57] ABSTRACT

This invention encompasses a pharmaceutical composition comprising an effective amount of alendronate salt for reducing calcium loss and an effective amount of a gastric propulsive agent, preferably cisapride, to prevent gastric reflux caused by the alendronate salt.

6 Claims, No Drawings

DRUG COMBINATION FOR TREATING CALCIUM LOSS

FIELD OF THE INVENTION

This invention is related to the field of reducing side effects of a drug. In particular it related to reducing side effects of drugs which reduce calcium loss.

DESCRIPTION OF THE PRIOR ART

Alendronate is an agent for reducing calcium resorption and thereby treating loss of calcium. Alendronate sodium is sold under the trademark Fosamax® by Merck & Co., Inc., West Point, Pa. 19486. Fosamax® has a side effect of producing severe gastric and esophageal distress. U.S. Pat. No. 4,705,651 describes the preparation of alendronate. U.S. Pat. No. 4,705,651 is incorporated herein by reference in its entirety. The pharmacological properties and dosage of Fosamax® is described in detail in the 1996 Supplement to Physicians Desk Reference. That reference is incorporated herein by reference.

Alendronate sodium, (4-amino-1-hydroxybutylidene) bis-phosphonic acid, monosodium salt has the following structure:

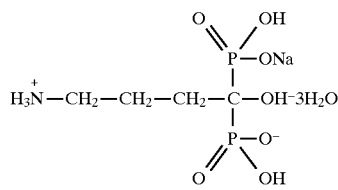

U.S. Pat. No. 4,962,115 describes cisapride and related gastric propulsive compounds. The entire specification of U.S. Pat. No. 4,962,115 is incorporated herein by reference. Cisapride is sold under the brand name PROPULSID® as an agent to promote gastric emptying. Cisapride, Cis 4-amino-5-chloro-N-[1-(3-p-fluorophenylpropyl]3-methoxy-4-pipemdinyl)-0-anisamide, has the following structure:

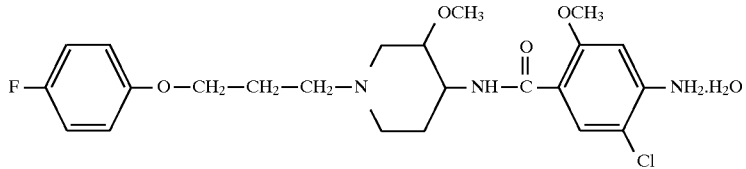

SUMMARY OF INVENTION

This invention encompasses a pharmaceutical composition comprising an effective amount of alendronate salt for reducing calcium loss and an effective amount of gastric propulsive agent to relieve and prevent esophageal and gastric distress.

The invention also encompasses a method for relieving and preventing esophageal and gastric distress caused by an alendronate salt which comprises administering to a patient treated with alendronate salt a gastric reflux inhibiting amount of a gastric propulsive agent, preferably cisapride, at or about the time of administering the alendronate salt.

DETAILED DESCRIPTION OF THE INVENTION

The inventor believes that the esophageal and gastric distress caused by alendronate is due to gastric reflux. Therefore, it is an object of this invention to provide an alendronate formulation which has a therapeutically effective amount of an alendronate salt to reduce calcium resorption and at the same time to have a therapeutically effective amount of a gastric propulsive agent to overcome the gastric reflux side effect of alendronate. Those skilled in the pharmaceutical arts will recognize that other gastric propulsive agents other than cisapride and compounds related to cisapride are also useable by separate administration or in combination with alendronate.

Alendronate is an agent for reducing calcium loss and is sold under the trademark Fosamax® by Merck & Co. This product has a side effect of producing severe esophagitis due to gastric reflux. The recommended daily dose of Fosamax® is about 10 mg/day. For Paget's disease the recommended dose is 40 mg/day. The present invention contemplates unit dose of between about 10 mg to 40 mg of alendronate salt.

Cisapride is available in 10 mg or 20 mg tablets under the tradename of PROPULSID®. A detailed description of this material is found in 1996 Physicians Desk Reference (PDR) at pages 1300–1301 which is incorporated herein by reference. Cisapride is combined with alendronate salt to reduce the side effect of gastric reflux. Analogs of cisapride and closely related compounds described in U.S. Pat. No. 4,962,115 are suitable gastric propulsive agents.

Alendronate is an agent for reducing calcium loss and is sold under the trademark Fosamax® by Merck & Co. This product has a side effect of producing severe esophagitis due to gastric reflux. The recommended daily dose of Fosamax® is about 10 mg/day. For Paget's disease the recommended dose is 40 mg/day. The present invention contemplates unit dose of between about 10 mg to 40 mg of alendronate salt.

A preferred dose is a tablet of 10 mg of alendronate sodium and 10 mg of cisapride in inactive carriers of microcrystallin cellulose, anhydrous lactose, croscarmellose sodium, and magnesium stearate.

What is claimed is:

1. A pharmaceutical composition comprising an effective amount of alendronate salt for reducing calcium loss and an effective amount of gastric propulsive agent to prevent gastric reflux caused by alendronate salt.

2. A pharmaceutical composition, according to claim 1, wherein the gastric propulsive drug is cisapride.

3. A pharmaceutical composition, according to claim 1, which contains 10 to 40 mg of alendronate sodium and 10 to 20 mg of cisapride.

4. A pharmaceutical composition, according to claim 3, which contains about 10 mg of alendronate sodium and about 10 mg of cisapride.

5. A method for preventing esophageal or gastric distress caused by an alendronate salt comprising administering to a patient treated with alendronate salt a gastric reflux inhibiting amount of a gastric propulsive drug at or about the time of administering the alendronate salt.

6. A method according to claim 5 wherein the gastric propulsive drug is cisapride.

* * * * *